United States Patent
Nam et al.

(10) Patent No.: US 11,591,718 B2
(45) Date of Patent: Feb. 28, 2023

(54) MAGNETIC-BASED BIOPANNING METHOD THROUGH ATTACHMENT OF MAGNETIC BEAD TO CELL

(71) Applicant: AIMED BIO INC., Seoul (KR)

(72) Inventors: Do-Hyun Nam, Seoul (KR); Byeongkwi Min, Seoul (KR)

(73) Assignee: AIMED BIO INC., Seoul (KR)

( * ) Notice: Subject to any disclaimer, the term of this patent is extended or adjusted under 35 U.S.C. 154(b) by 135 days.

(21) Appl. No.: 17/041,641

(22) PCT Filed: Apr. 26, 2019

(86) PCT No.: PCT/KR2019/005080
§ 371 (c)(1),
(2) Date: Sep. 25, 2020

(87) PCT Pub. No.: WO2019/209073
PCT Pub. Date: Oct. 31, 2019

(65) Prior Publication Data
US 2021/0123162 A1     Apr. 29, 2021

(30) Foreign Application Priority Data
Apr. 27, 2018    (KR) .................. 10-2018-0049100

(51) Int. Cl.
C40B 30/04      (2006.01)
C07K 16/00      (2006.01)
(Continued)

(52) U.S. Cl.
CPC ............. *C40B 30/04* (2013.01); *C07K 16/00* (2013.01); *C40B 40/02* (2013.01); *G01N 33/554* (2013.01); *G01N 33/6854* (2013.01)

(58) Field of Classification Search
None
See application file for complete search history.

(56) References Cited

U.S. PATENT DOCUMENTS

| 4,554,101 A | 11/1985 | Hopp |
| 5,876,925 A | 3/1999 | Siegel |
| 8,728,747 B2 | 5/2014 | Shirwan |

FOREIGN PATENT DOCUMENTS

| JP | 2004248666 A | 9/2004 |
| JP | 2017164284 A | 9/2017 |

(Continued)

OTHER PUBLICATIONS

Min, B., et al., "Semi-Automated Cell Panning for Efficient Isolation of FGFR3-Targeting Antibody", International Journal of Molecular Sciences, 2021, Page(s) https://doi.org.10.3390/ijms22126240, vol. 22, No. 6240, Publisher: MDPI.

(Continued)

*Primary Examiner* — Christian C Boesen
(74) *Attorney, Agent, or Firm* — Hultquist, PLLC; Steven J. Hultquist

(57) ABSTRACT

The present invention relates to a method for screening an antibody or antigen-binding fragment thereof by using cells bearing magnetic beads and, more particularly, to a method for screening an antibody binding specifically to an antigen protein or an antigen-binding fragment thereof, in which cells having biotinylated phospholipids in the cell membranes thereof and a streptavidin-magnetic bead complex fused to the surfaces thereof, and a magnetic-based system are utilized.

10 Claims, 17 Drawing Sheets
(16 of 17 Drawing Sheet(s) Filed in Color)

(51) Int. Cl.
　　　*C40B 40/02*　　(2006.01)
　　　*G01N 33/554*　　(2006.01)
　　　*G01N 33/68*　　(2006.01)

(56) References Cited

FOREIGN PATENT DOCUMENTS

| KR | 1020110027848 A | 3/2011 |
| KR | 1020150028225 A | 3/2015 |
| WO | 2017042242 A1 | 3/2017 |

OTHER PUBLICATIONS

Yoon, H., et al., "An efficient strategy for cell-based antibody library selection using an integrated vector system", BMC Biotechnology, 2012, Page(s) http://www.biomedcentral.om/1472-6750/12/62, vol. 12, No. 62, Publisher: BioMed Central.

Henry, S., et al., "Rapid One-Step Biotinylation of Biological and Non-Biological Surfaces", "Scientific Reports", Feb. 12, 2018, pp. 1-6, vol. 8, No. 2845.

McGuire, M., et al., "Biopanning of Phage Displayed Peptide Libraries for the Isolation of Cell-Specific Ligands", "Method Mol. Biol.", 2009, pp. 291-321, vol. 504.

Pavoni, E., et al., "Optimized Selection of Anti-Tumor Recombinant Antibodies from Phage Libraries on Intact Cells", "Molecular Immunology", 2014, pp. 317-322, vol. 57.

Suharni, Y., et al., "Proteoliposome-based Selection of a Recombinant Antibody Fragment Against the Human M2 Muscarnic Acetylcholine Receptor", "Monoclonal Antibodies in Immunodiagnosis and Immunotherapy", Nov. 6, 2014, pp. 378-385, vol. 33, No. 6.

Tjandra, J., et al., "Development of Human Anti-Murine Antibody (HAMA) Response in Patients", "Immunol. Cell Biol.", 1990, pp. 367-376, vol. 68.

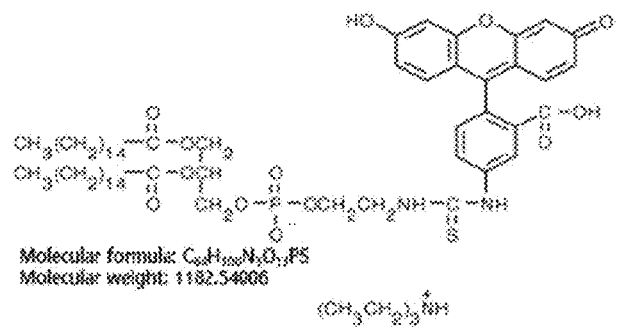
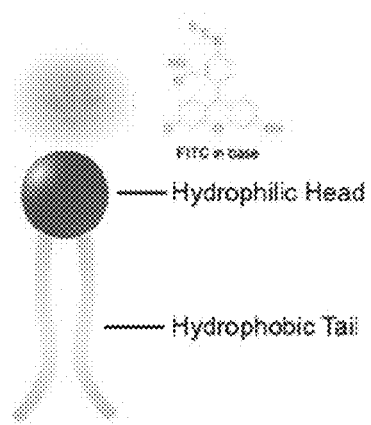
FIG. 2A  FIG. 2B
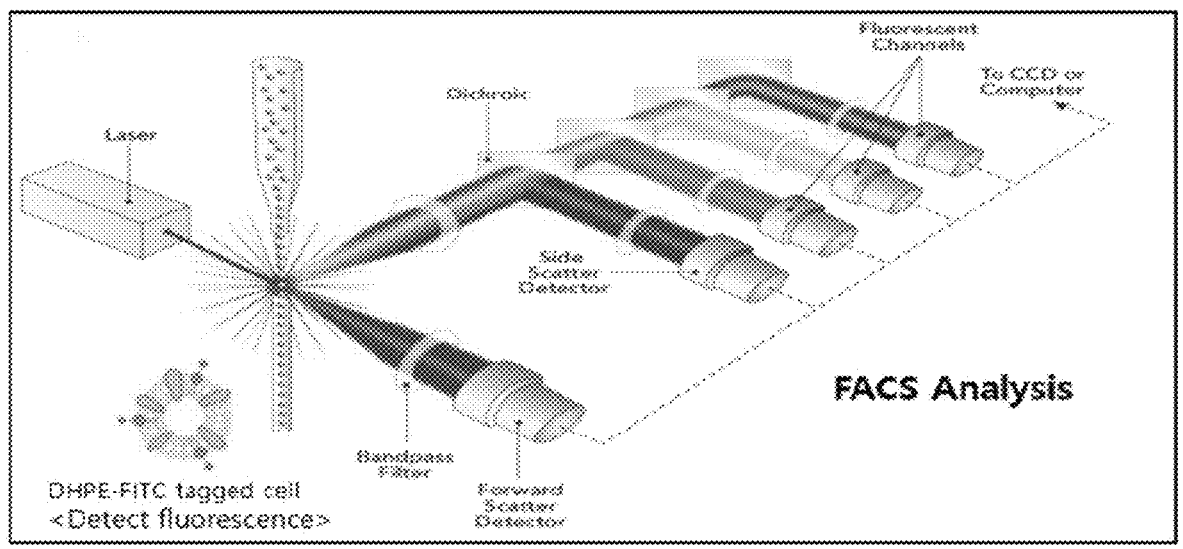
FIG. 2C

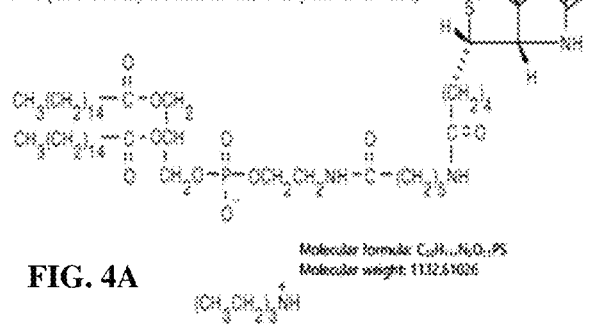
FIG. 4A
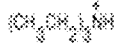
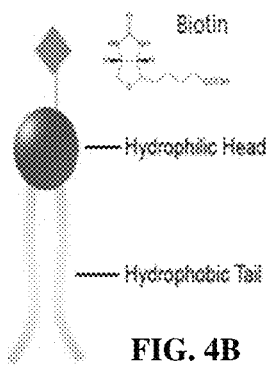
FIG. 4B
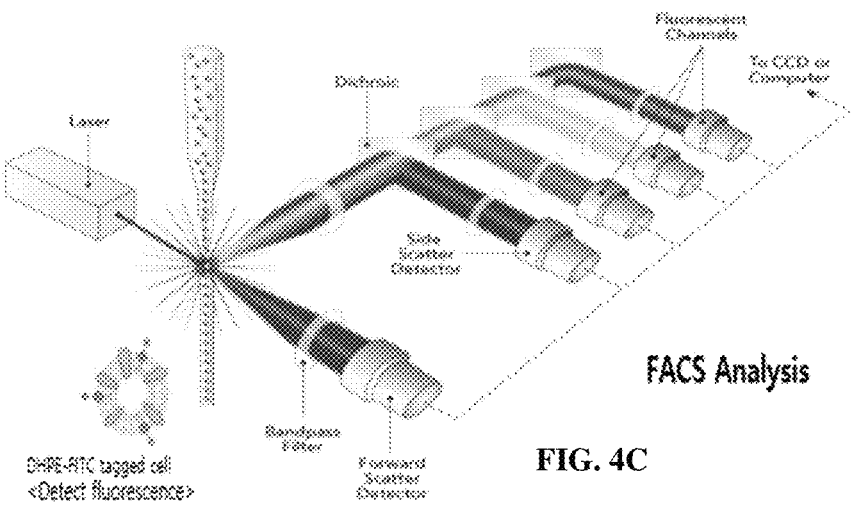
FIG. 4C

The result of comparing the two methods under the same experimental conditions showed that the direct method is capable of attaching magnetic beads to a larger amount of cells.

Reagent info

| Home | | 24 DW plate | |
|---|---|---|---|
| Name | Well volume [µl] | Total reagent volume [µl] | Type |
| - | - | - | - |

| waste | | 24 DW plate | |
|---|---|---|---|
| Name | Well volume [µl] | Total reagent volume [µl] | Type |
| waste | 1000 | - | Reagent |

| Phage Plate | | 24 DW plate | |
|---|---|---|---|
| Name | Well volume [µl] | Total reagent volume [µl] | Type |
| Phage stock | 1000 | - | Reagent |

| Wash-1 | | 24 DW plate | |
|---|---|---|---|
| Name | Well volume [µl] | Total reagent volume [µl] | Type |
| PBS | 1000 | - | Reagent |

| Wash-2 | | 24 DW plate | |
|---|---|---|---|
| Name | Well volume [µl] | Total reagent volume [µl] | Type |
| PBS | 1000 | - | Reagent |

| Wash-3 | | 24 DW plate | |
|---|---|---|---|
| Name | Well volume [µl] | Total reagent volume [µl] | Type |
| PBS | 1000 | - | Reagent |

| Elution plate | | 24 DW plate | |
|---|---|---|---|
| Name | Well volume [µl] | Total reagent volume [µl] | Type |
| Elution buffer(Low-PH buffer) | 1000 | - | Reagent |

| Cell lysis plate | | 24 DW plate | |
|---|---|---|---|
| Name | Well volume [µl] | Total reagent volume [µl] | Type |
| 100mM Triethylamine(or Lysis-M) | 500 | - | Reagent |

FIG. 14A Results of panning of magnetic-bead-attached cells using phage pool obtained by 4$^{th}$-round recombinant protein fixation (immunotube)

[Low wash condition]

| 1$^{st}$-round automatic cell panning | | PDC#1 |
|---|---|---|
| | input | 1.95E+11 |
| | output | 1.88E+07 |
| | ratio | 9.64E-05 |

[High wash condition]

| 1$^{st}$-round automatic cell panning | | PDC#1 |
|---|---|---|
| | input | 4.90E+11 |
| | output | 1.30E+06 |
| | ratio | 2.65E-06 |

FIG. 14B Results of automated panning of magnetic-bead-attached cells using phage pool obtained by 4$^{th}$-round automated panning using magnetic-bead-attached recombinant protein

[Low wash condition]

| 1$^{st}$-round automatic cell panning | | PDC#1 |
|---|---|---|
| | input | 1.83E+12 |
| | output | 5.61E+07 |
| | ratio | 3.07E-05 |

FIG. 15A  Results of panning of magnetic-bead-attached cells using phage pool obtained by 4$^{th}$-round recombinant protein fixation (immunotube)

| Cell | Wash condition | Screening | Positive clones | Novel sequences |
|---|---|---|---|---|
| PDC#1 | Low | 188 | 3 | 2 |
| PDC#1 | High | 184 | 4 | 3 |

FIG. 15B  Results of automated panning of magnetic-bead-attached cells using phage pool obtained by 4$^{th}$-round automated panning using magnetic-bead-attached recombinant protein

| Cell | Wash condition | Screening | Positive clones | Novel sequences |
|---|---|---|---|---|
| PDC#1 | Low | 94 | 2 | 2 |

MAGNETIC-BASED BIOPANNING METHOD THROUGH ATTACHMENT OF MAGNETIC BEAD TO CELL

CROSS-REFERENCE TO RELATED APPLICATIONS

This is a U.S. national phase under the provisions of 35 U.S.C. § 371 of International Patent Application No. PCT/KR19/05080 filed Apr. 26, 2019, which in turn claims priority under 35 U.S.C. § 119 of Korean Patent Application No. 10-2018-0049100 filed Apr. 27, 2018. The disclosures of such international patent application and Korean patent application are hereby incorporated herein by reference in their respective entireties, for all purposes.

TECHNICAL FIELD

The present invention relates to a method of screening an antibody or antigen-binding fragment thereof using cells having magnetic beads attached thereto, and more specifically, to a method for screening an antibody or antigen-binding fragment thereof specifically binding to an antigenic protein with a magnetism-based system using cells containing a phospholipid/biotin/streptavidin/magnetic-bead complex on the surface thereof and overexpressing an antigenic protein.

BACKGROUND ART

In 1975, technology for developing monoclonal antibodies began with hybridoma technology. Hybridoma technology is technology for selecting monoclonal antibodies by inducing an immune response in mice and then fusing B cells with myeloma cells and maintaining an immortal state. This technology involves obtaining a mouse antibody and thus has a side effect in that the mouse antibody is recognized as an antigen, when applied to humans, thus causing an immune response. This is called "HAMA" (human anti-mouse antibody response) (Tiandra J. J. et al., Immunol. Cell Biol., Vol. 66, pp. 367-76, 1990).

In order to overcome the side effects, a chimeric antibody and a humanized antibody were developed by applying a technique that transforms mouse antibodies, similar to human antibodies. However, there are still problems in that immune responses occur and development time is considerably long.

Phage display technology for expressing proteins or peptides on the surfaces of bacteriophages was developed in 1985. Phage display is a method of producing a phage library having various antibody fragments and using the phage library for antibody selection, and is continuously used by developers owing to the fast selection speed and relatively simple application thereof.

Antibodies are selected through a method of selecting, recovering and amplifying antibody fragments specific to a desired antigen using the phage library, which is called "biopanning". There are various typical methods of panning, including panning using recombinant proteins, cell panning, magnetic bead-based panning, panning in vivo, and panning using tissue (McGuire M. J. et al., Method Mol. Biol., Vol. 504, pp. 291-321, 2009).

Panning using recombinant proteins is generally used, but disadvantageously has a limitation of an antibody library for a specific antigen and requires a purified antigen with high purity. With the purified protein, it is difficult to realize post translation modification (PTM) of the protein, so even if an antibody is discovered, it may not actually work in vivo.

To overcome this, cell panning was developed, and it has become easier to develop antibodies that bind to specific membrane proteins (G protein coupled receptors, ligand-gated ion channels, receptor tyrosine kinases, and immunoglobulin-like receptors). This method uses a native form of cells as antigens and thus is capable of selecting antibodies in a form realizing the three-dimensional structure and the PTM of the protein.

However, cell panning is labor-intensive and may exhibit great difference among users in experiments. Thus, there is a need for next-generation cell panning that is capable of solving and overcoming these problems.

Various diagnostic and therapeutic antibodies have been developed to date through phage display, and high-speed mass screening system methods fused with an automated system are also being developed in order to establish a rapid and accurate panning method.

Accordingly, as a result of extensive efforts to develop a method for screening antibodies at a high speed and high volume, the present inventors found that antibodies can be selected at high speed, sensitivity and accuracy while reducing side effects by screening an antibody library using a magnetism-based system and cells containing magnetic beads and antigenic proteins, thus completing the present invention.

The information disclosed in this Background section is provided only for enhancement of understanding of the background of the present invention, and therefore it may not include information that forms the prior art that is already obvious to those skilled in the art.

DISCLOSURE

It is one object of the present invention to provide a method for screening an antibody using a magnetism-based system and cells including magnetic beads on the surface thereof and overexpressing an antigenic protein.

In accordance with an aspect of the present invention, the above and other objects can be accomplished by the provision of a method for screening an antibody or antigen-binding fragment thereof binding to an antigenic protein, the method including: (i) preparing a cell overexpressing an antigenic protein, wherein a biotinylated phospholipid is inserted into a membrane of the cell and the biotinylated phospholipid is bound to a streptavidin/magnetic-bead complex; (ii) treating the cell with a library including an antibody or antigen-binding fragment thereof and screening an antibody or antigen-binding fragment thereof binding to the antigen protein using a magnetism-based system; (iii) reacting the screened antibody or antigen-binding fragment library thereof with cells not expressing the antigen protein to select only an antibody or antigen-binding fragment thereof specifically binding to the antigen protein; and (iv) separating and/or removing an antibody or antigen-binding fragment thereof binding to an antigen other than the antigenic protein from the selected antibody or antigen-binding fragment thereof.

DESCRIPTION OF DRAWINGS

The patent or application file contains at least one drawing executed in color. Copies of this patent or patent application publication with color drawing(s) will be provided by the Office upon request and payment of the necessary fee.

FIG. 2A shows the chemical formula of DHPE-FITC used in an embodiment of the present invention, FIG. 2B is a schematic diagram of the material, and FIG. 2C is a schematic diagram illustrating a process of separating cells according to an embodiment of the present invention through FACS analysis.

FIG. 4A shows the chemical formula of B-X-DHPE used in an embodiment of the present invention, FIG. 4B is a schematic diagram of the material, and FIG. 4C is a schematic diagram illustrating a process of separating cells according to an embodiment of the present invention through FACS analysis.

FIG. 13A shows a summary of reagents required for panning magnetic bead-attached cells using a magnetism-based device, and FIG. 13B shows a summary of a protocol for panning magnetic bead-attached cells using a magnetism-based device (BindIt Software 3.3.1 for KingFisher Instruments).

FIG. 14A shows results of automatic panning of cells derived from a patient overexpressing a specific antigen using a magnetism-based device, wherein the output of bio-panning through an antigen-immobilization method is used and the result is obtained under strong and weak washing conditions, and FIG. 14B shows results of automatic panning of cells derived from a patient overexpressing a specific antigen using a magnetism-based device, wherein the output of bio-panning through a magnetic-bead-attached antigen is used and the result is obtained under weak washing conditions.

FIG. 15A shows results of ELISA-based antibody screening having binding ability specific to a certain antigen using the output of automatic panning, wherein the output of bio-panning through an antigen immobilization method is used and the result is obtained under strong and weak washing conditions, and FIG. 15B shows results of ELISA-based antibody screening having binding ability specific to a certain antigen using the output of automatic panning, wherein the output of bio-panning through a magnetic-bead-attached antigen is used and the result is obtained under weak washing conditions.

BEST MODE

Unless defined otherwise, all technical and scientific terms used herein have the same meanings as appreciated by those skilled in the field to which the present invention pertains. In general, the nomenclature used herein is well-known in the art and is ordinarily used.

The present inventors have endeavored to overcome the drawback in which cell panning results differ greatly among users. As a result, the present inventors tried to confirm that, when cell panning is performed in a magnetism-based system using cells containing magnetic beads, the efficiency of cell panning is increased and high-speed mass screening is possible.

In addition, the present inventors made efforts to develop antibodies for anticancer treatment using cells derived from patients having antigenic proteins in order to select antibodies that have a high possibility of successful use in future clinical trials and that are internalized and can act effectively inside cells. As a result, the present inventors have selected antibodies that bind to antigenic proteins with high affinity and are internalized into cells using phage display technology, and confirmed that these antibodies are internalized into cells.

Figure 12:
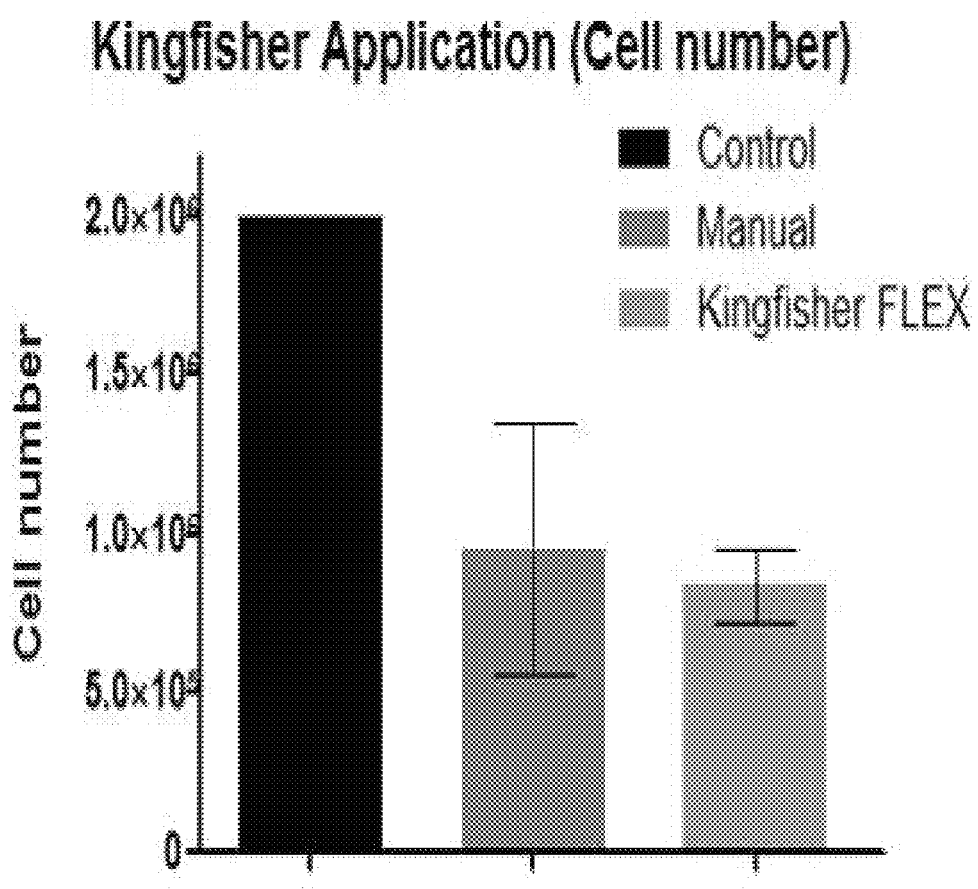
FIG. 12 shows a result of comparison of the number of cells remaining after the final step when conducting automatically panning by applying to a magnetism-based device after formation of a phospholipid/biotin/streptavidin/magnetic-bead complex of the cell according to an embodiment of the present invention, with a manual panning method.

Accordingly, in an embodiment of the present invention, cell panning was performed using cells containing a biotin-bound phospholipid on a cell membrane and containing a streptavidin/magnetic-bead complex on the surface thereof. As a result, it was possible to screen antibodies at a high speed (FIG. 12).

Therefore, in one aspect, the present invention provides a method for screening an antibody or antigen-binding fragment thereof binding to an antigenic protein, the method including: (i) preparing a cell overexpressing an antigenic protein, wherein a biotinylated phospholipid is inserted into a membrane of the cell and the biotinylated phospholipid is bound to a streptavidin/magnetic-bead complex; (ii) treating the cell with a library including an antibody or antigen-binding fragment thereof, and screening an antibody or antigen-binding fragment thereof binding to the antigen protein using a magnet-based system; (iii) reacting the screened antibody or antigen-binding fragment library thereof with cells not expressing the antigen protein to thereby select only an antibody or antigen-binding fragment thereof specifically binding to the antigen protein; and (iv) separating and removing an antibody or antigen-binding fragment thereof binding to an antigen other than the antigenic protein from the selected antibody or antigen-binding fragment thereof.

The term "antibody" as used herein means an immunoglobulin selected from the group consisting of IgA, IgE, IgM, IgD, IgY and IgG, and can specifically bind to a target antigen. It consists of two light chains and two heavy chains, and each chain includes a variable domain having a variable amino acid sequence and a constant domain having a constant amino acid sequence. An antigen-binding site is located at the end of the three-dimensional structure of the variable domain, and this site is formed by combining three complementarity-determining regions present in each of the light and heavy chains. The complementarity-determining region is a part having particularly high variability in amino acid sequence among the variable domains, and antibodies specific for various antigens can be found due to such high variability. The scope of the present invention includes not only a complete antibody form, but also an antigen-binding fragment of the antibody molecule.

As used herein, the term "ScFv" (single-chain Fv, single-chain fragment antibody or antibody fragment) refers to an antibody in which the variable domains of the light and heavy chains are linked. In some cases, ScFv may include a linker (linking site) consisting of a peptide chain having about 15 linked amino acids, and in this case, ScFv may have a structure including a light-chain variable domain, a linking site, and a heavy-chain variable domain, or including a heavy-chain variable domain, a linked site, and a light-chain variable domain, and has antigen specificity the same as or similar to that of the original antibody.

The term "complete antibody" refers to a structure having two full-length light chains and two full-length heavy chains, wherein each light chain is linked to a corresponding heavy chain by a disulfide bond. The heavy-chain constant domain has gamma (γ), mu (μ), alpha (α), delta (δ) and epsilon (ε) types, and is subclassified into gamma 1 (γ1), gamma 2 (γ2), gamma 3 (γ3), gamma 4 (γ4), alpha 1 (α1) and alpha 2 (α2). The constant domain of the light chain has kappa (κ) and lambda (λ) types.

The antigen-binding fragment of an antibody or antibody fragment refers to a fragment that has antigen-binding capacity, and includes Fab, F(ab'), F(ab')2, Fv and the like. Among the antibody fragments, Fab refers to a structure including a variable domain of each of the heavy chain and the light chain, the constant domain of the light chain, and the first constant domain (CH1) of the heavy chain, each having one antigen-binding site. Fab' is different from Fab in that it further includes a hinge region including at least one cysteine residue at the C-terminus of the CH1 domain of the heavy chain. F(ab')2 is created by a disulfide bond between cysteine residues in the hinge region of Fab'. Fv is the minimal antibody fragment having only a heavy-chain variable domain and a light-chain variable domain, and recombinant technology for producing Fv is disclosed in PCT International Publications such as WO 88/10649, WO 88/106630, WO 88/07085, WO 88/07086 and WO 88/09344. A two-chain Fv is a fragment wherein the variable domain of the heavy chain and the variable domain of the light chain are linked by a non-covalent bond, and a single-chain Fv (scFv) is a fragment wherein the variable domain of the heavy chain and the variable domain of the light chain are generally linked by a covalent bond via a peptide linker therebetween, or are directly linked at the C-terminus, forming a dimer-shaped structure, like the two-chain Fv. Such antibody fragments may be obtained using proteases (e.g., Fab can be obtained by restriction-cleaving the whole antibody with papain, and the F(ab')2 fragment can be obtained by restriction-cleaving the whole antibody with pepsin), and may be prepared using genetic recombination techniques.

As used herein, the term "antibody (or ScFv) library" refers to a collection of various antibody genes having different sequences. In order to separate antibodies specific for any antigen from the antibody library, very high diversity is required, and a library consisting of different antibody clones is constructed and used. The antibody genes constituting such an antibody library may be cloned into, for example, a phagemid vector and transformed into a transformant (E. coli).

As used herein, the term "nucleic acid" may be used interchangeably with "gene" or "nucleotide", and may be, for example, selected from the group consisting of natural/synthetic DNA, genomic DNA, natural/synthetic RNA, cDNA and cRNA, but is not limited thereto.

As used herein, the term "phagemid" vector refers to a plasmid DNA that is used for phage display and has a phage origin of replication, and generally has an antibiotic resistance gene as a selection marker. The phagemid vector used for phage display includes the gIII gene of the M13 phage or a portion thereof, and the ScFv gene is ligated to the 5' end of the gIII gene and is expressed through a transformant.

As used herein, the term "helper phage" refers to a phage that provides the necessary genetic information so that the phagemid is packaged into phage particles. Since only gIII of the phage genes or a portion thereof are present in the phagemid, host cells (transformants) transformed with the phagemid are infected with a helper phage to thereby supply the remaining phage genes. There are types such as M13K07 or VCSM13, and most of them include antibiotic resistance genes such as kanamycin, so that transformants infected with the helper phage can be selected. In addition, because the packaging signal is defective, phagemid genes are selectively packaged into phage particles rather than helper phage genes.

As used herein, the term "signal sequence" refers to a base sequence or an amino acid sequence corresponding thereto, which is located at the 5' end of a gene and functions as a necessary signal when the protein encoded from the gene is secreted to the outside.

As used herein, the term "phage display" is a technique for displaying a mutant polypeptide as a fusion protein with at least a part of a coat protein, for example, on the surface of the particle of a phage, for example, a fibrous phage. The usefulness of phage display is to rapidly and efficiently classify sequences that bind to target antigens with high affinity in large libraries of randomized protein mutants. Displaying peptides and protein libraries on phages has been used to screen millions of polypeptides in order to identify polypeptides with specific binding properties.

Phage display technology has offered a powerful tool for generating and screening novel proteins that bind to specific ligands (e.g., antigens). Using phage display technology, large libraries of protein mutants can be generated, and sequences binding with high affinity to target antigens can be rapidly classified. The nucleic acid encoding mutant polypeptides is fused with a nucleic acid sequence encoding a viral coat protein, e.g., a gene III or gene VIII protein. A monophasic phage display system, in which a nucleic acid sequence encoding a protein or polypeptide is fused with a nucleic acid sequence encoding a part of the gene III protein, has been developed. In the monophasic display system, a fused gene is expressed at a low level and a wild-type gene III protein is also expressed, and thus particle infectivity is maintained.

It is important to demonstrate the expression of peptides on the fibrous phage surface and the expression of functional antibody fragments in the peripheral cytoplasm of E. coli for the development of antibody phage display libraries. Libraries of antibody- or antigen-binding polypeptides are prepared by a number of methods, for example, methods of modifying a single gene by inserting a random DNA sequence or cloning a related gene sequence. The libraries can be screened for the expression of antibody- or antigen-binding proteins having desired characteristics.

Phage display technology has several advantages over conventional hybridomas and recombinant methods for producing antibodies having desired characteristics. This technique provides the generation of large antibody libraries with a variety of sequences within a short time without using animals. The production of hybridomas and the production of humanized antibodies may require a production time of several months. In addition, since no immunity is required, the phage antibody libraries can generate antibodies against antigens that are toxic or have low antigenicity. The phage antibody libraries can also be used to produce and identify novel therapeutic antibodies.

Techniques for generating human antibodies from immunized humans, non-immunized humans, germline sequences, or unsensitized B-cell Ig repertoires using phage display libraries can be used. Various lymphatic tissues can be used to prepare unsensitized or non-immunogenic antigen-binding libraries.

Techniques for identifying and separating high-affinity antibodies from phage display libraries are important for the separation of new therapeutic antibodies. The separation of high-affinity antibodies from the libraries depends on the size of the libraries, the production efficiency in bacterial cells, and the variety of libraries. The size of the libraries is reduced by inefficient folding of the antibody- or antigen-binding protein and inefficient production due to the presence of the stop codon. Expression in bacterial cells can be inhibited when the antibody- or antigen-binding domain is not properly folded. Expression can be improved by alternately mutating residues on the surface of the variable/constant interfaces or the selected CDR residues. The sequence of the framework region is an element to provide appropriate folding when generating antibody phage libraries in bacterial cells.

It is important to generate various libraries of antibody- or antigen-binding proteins in the separation of high-affinity antibodies. CDR3 regions have often been found to participate in antigen binding. Since the CDR3 region on the heavy chain varies considerably in terms of size, sequence and structurally dimensional morphology, various libraries can be prepared using the same.

Also, diversity can be created by randomizing the CDR regions of variable heavy and light chains using all 20 amino acids at each position. The use of all 20 amino acids results in antibody sequences with great diversity and an increased chance of identifying new antibodies.

The antibody of the present invention includes, but is not limited to, monoclonal antibodies, multispecific antibodies, human antibodies, humanized antibodies, chimeric antibodies, single-chain FVs (scFVs), single-chain antibodies, Fab fragments, F(ab') fragments, disulfide-linked FVs (sdFVs), anti-idiotypic (anti-Id) antibodies, epitope-binding fragments of the antibodies, or the like.

The term "monoclonal antibody" refers to an identical antibody, which is obtained from a population of substantially homogeneous antibodies, that is, each antibody constituting the population, excluding possible naturally occurring mutations that may be present in small amounts. Monoclonal antibodies are highly specific and are induced against a single antigenic site.

A "humanized"-type non-human (e.g., murine) antibody refers to a chimeric antibody that contains a minimal sequence derived from non-human immunoglobulin. In most cases, the humanized antibody is a human immunoglobulin (acceptor antibody) in which a residue from the hypervariable region of an acceptor is replaced with a residue from the hypervariable region of a non-human species (donor antibody) having the desired specificity, affinity and capability, such as a mouse, rat, rabbit or non-human primate.

The term "human antibody" means a molecule derived from human immunoglobulin, wherein all of the amino acid sequences constituting the antibody including a complementarity-determining region and a structural region are composed of human immunoglobulin.

A part of the heavy chain and/or light chain is identical to or homologous with the corresponding sequence in an antibody derived from a particular species or belonging to a particular antibody class or subclass, while the other chain(s) include "chimeric" antibodies (immunoglobulins) which are identical to or homologous with corresponding sequences in an antibody derived from another species or belonging to another antibody class or subclass, as well as fragments of such antibody exhibiting the desired biological activity.

As used herein, the term "antibody variable domain" refers to the light- and heavy-chain regions of an antibody molecule including the amino acid sequences of a complementarity-determining region (CDR; i.e., CDR1, CDR2, and CDR3) and a framework region (FR). VH refers to a variable domain of the heavy chain. VL refers to a variable domain of the light chain.

The term "complementarity-determining region" (CDR; i.e., CDR1, CDR2, and CDR3) refers to an amino acid residue of the antibody variable domain that is necessary for antigen binding. Each variable domain typically has three CDR regions, identified as CDR1, CDR2, and CDR3.

The term "framework region" (FR) refers to a variable domain residue other than a CDR residue. Each variable domain typically has four FRs, identified as FR1, FR2, FR3, and FR4.

As used herein, the term "biotin" refers to a water-soluble B-vitamin (vitamin B7) also referred to as vitamin H or coenzyme R. The biotin includes a ureido (tetrahydroimidizalone) ring fused with a tetrahydrothiophene ring.

Biotin includes valeric acid bound to one carbon atom of a tetrahydrothiophene ring. Biotin is a coenzyme for the carboxylase enzyme, and is involved in the synthesis of fatty acids, isoleucine, and valine, as well as in gluconeogenesis. In addition to the above-described characteristics as the coenzyme, biotin has a dissociation constant Kd of $10^{-14}$ to $10^{-15}$ M, and has a strong binding capacity to proteins such as avidin, streptavidin, and neutravidin (or deglycosylated avidin; neutravidin or deglycosylated avidin). In particular, since the specific binding to streptavidin can be maintained even under very harsh conditions, streptavidin-biotin binding has been variously applied in the field of biotechnology. Since biotin is small in size and does not affect the activity of physiologically active substances such as proteins including the same, it can be bound to various physiologically active substances and thus used for biochemical assays. This process, that is, a process of binding biotin to the physiologically active substance, is called "biotinylation".

In the present invention, the phospholipid includes any one selected from the group consisting of PE (phosphoethanolamine)-based phospholipids, PA (phosphatidic acid)-based phospholipids, PG (phosphatidylglycerol)-based phospholipids, PS (phosphatidylserine)-based phospholipids, PI (phosphatidylinositol)-based phospholipids, sphingolipid-based phospholipids and sterol-based phospholipids, but is not limited thereto.

In the present invention, the phospholipid includes any one selected from the group consisting of DHPE (1,2-dihexadecanoyl-sn-glycero-3-phosphoethanolamine), fluorescein DHPE (N-(fluoresceine-5-thiocarbamoyl)-1-2-dihexadecanoyl-sn-glycero-3-phosphoethanolamine), B-X DHPE (N-((6-(biotinoyl)amino)hexanoyl)-1-2-dihexadecanoyl-sn-glycero-3-phosphoethanolamine), biotin PS (1-oleoyl-2-(12-biotinyl(aminododecanoyl))-sn-glycero-3-phospho-L-serine (ammonium salt)), and biotin PC (1-oleoyl-2-[12-biotinyl(aminododecanoyl)]-sn-glycero-3-phosphocholine), but is not limited thereto.

In the present invention, the cell overexpressing an antigenic protein, in which biotinylated phospholipid is inserted into the cell membrane and the biotinylated phospholipid is bound to the streptavidin/magnetic bead complex, may be prepared by the process including: (a) culturing a cell overexpressing an antigen protein in the presence of biotinylated phospholipid to obtain a cell in which the biotinylated phospholipid is inserted into the cell membrane; and (b) treating the biotinylated phospholipid of the obtained cell with a streptavidin/magnetic-bead complex to obtain a cell in which the biotinylated phospholipid is inserted into the cell membrane and in which the biotinylated phospholipid is bound to the streptavidin/magnetic-bead complex.

In the present invention, the cell overexpressing an antigenic protein, in which a biotinylated phospholipid is inserted into the cell membrane and the biotinylated phospholipid is bound to the streptavidin/magnetic-bead complex, may be prepared through a process including: (a) reacting biotinylated phospholipid with streptavidin and magnetic beads) to prepare a phospholipid/biotin/streptavidin/magnetic-bead complex; and (b) fusing the phospholipid/biotin/streptavidin/magnetic-bead complex to a cell overexpressing an antigen protein to obtain a cell overexpressing an antigen protein in which the biotinylated phospholipid is inserted into the cell membrane and in which the biotinylated phospholipid is bound to the streptavidin/magnetic-bead complex.

In the present invention, the cell may be fused with the streptavidin/magnetic-bead complex in a medium containing a surfactant.

In the present invention, the surfactant includes any one selected from the group consisting of alkyl polyglycoside, cetyl alcohol, decyl glucoside, decyl polyglucoside, maltosides, NP-40, oleyl alcohol, poloxamer, polysorbate, sorbitan, Triton X-100 and Tween 80, but is not limited thereto.

In the present invention, the magnetism-based system is a device for separating cells using magnetism, and is preferably KingFisher Flex™, but is not limited thereto.

In the present invention, the antibody or antigen-binding fragment thereof may be an antibody or antigen-binding fragment thereof that is internalized into a cell.

The present invention also includes (ii) treating the cell including magnetic beads and overexpressing an antigenic protein with a library including an antibody or an antigen-binding fragment thereof to screen an antibody or antigen-binding fragment thereof binding to the antigenic protein.

The method of measuring the antigen protein content of the overexpressing cells and normal cells may be carried out by measuring and comparing the expression level of the gene or protein encoding the antigen protein, and is preferably performed by one or more methods selected from the group consisting of FACS, ELISA, whole-exome sequencing and RNA sequencing, but is not limited thereto.

The method according to the present invention further includes (iii) treating cells not expressing the antigen protein with the screened antibody or antigen-binding fragment library thereof to thereby select only an antibody or antigen-binding fragment thereof specifically binding to the antigen protein.

The step (iii) is a step of conducting negative selection on the antibody or antigen-binding fragment thereof selected in step (ii), and enables screening an antibody having high selectivity for an antigen.

In the present invention, the cell that is removed so that the antigenic protein of step (iii) is not expressed may be a cell that does not naturally express the antigenic protein, or may be a patient-derived cell that is artificially manipulated so that the antigenic protein is not expressed. The artificial manipulation method may be any method that is capable of preventing the antigenic protein from being expressed, but is preferably carried out through treatment with at least one selected from the group consisting of an aptamer, siRNA, single-stranded siRNA, microRNA, and shRNA which bind to the antigenic protein.

In the present invention, the step of selecting only the antibody that binds to the antigen protein using the patient-derived cell not expressing the antigenic protein is negative screening, which is performed immediately after positive screening and has an effect of improving the accuracy of the selected antibody for the antigen protein.

The present invention further includes separating and/or removing an antibody or antigen-binding fragment thereof that binds to an antigen other than an antigenic protein from the selected antibody or antigen-binding fragment thereof.

The separation and/or removal may be carried out using electrophoresis, centrifugation, gel filtration, precipitation, dialysis, chromatography (such as ion exchange chromatography, affinity chromatography, immunosorbent chromatography, size exclusion chromatography), isoelectric focusing, various modifications and combinations thereof, and the like, but are not limited thereto.

The separation and/or removal may be carried out by removing impurities by, for example, centrifugation or ultrafiltration and purifying the result using, for example, affinity chromatography. Additional purification techniques such as anion or cation exchange chromatography, hydrophobic interaction chromatography, hydroxylapatite chromatography and the like may be used.

The antibody or binding fragment thereof selected by the present invention may be, for example, an IgG form, a Fab' fragment, an F(ab')2 fragment, a Fab fragment, an Fv fragment, or a single-chain Fv fragment (scFv), but is preferably produced in the form of IgG.

In another aspect, the present invention is directed to an antibody or antigen-binding fragment thereof screened by the above method.

The antibody or antibody fragment of the present invention may include not only an antibody but also biological equivalents thereto, as long as it can specifically recognize an antigen protein. For example, additional variations can be made to the amino acid sequence of the antibody in order to further improve the binding affinity and/or other biological properties of the antibody. Such variations include, for example, deletion, insertion and/or substitution of the amino acid sequence residues of the antibody. Such amino acid mutations are based on the relative similarity of amino-acid side-chain substituents, such as the hydrophobicity, hydrophilicity, charge and size thereof. It can be seen through analysis of the size, shape and type of amino-acid side-chain substituents that all of arginine, lysine and histidine are positively charged residues; alanine, glycine and serine have similar sizes; and phenylalanine, tryptophan and tyrosine have similar shapes. Thus, based on these considerations, arginine, lysine and histidine; alanine, glycine and serine; and phenylalanine, tryptophan and tyrosine are considered to be biologically functional equivalents.

The hydropathic index of amino acids may be considered when introducing mutations. Each amino acid has a hydrophobicity index assigned depending on the hydrophobicity and charge thereof as follows: isoleucine (+4.5); valine (+4.2); leucine (+3.8); phenylalanine (+2.8); cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The hydrophobic amino acid index is very important in eliciting the interactive biological function of a protein. It is a known fact that substitution with an amino acid having a similar hydrophobicity index is required in order to retain similar biological activity. When introducing a mutation with reference to the hydrophobicity index, substitution is conducted between amino acids showing a difference in the hydrophobicity index, preferably within ±2, more preferably within ±1, and even more preferably within ±0.5.

Meanwhile, it is also well known that substitutions between amino acids having similar hydrophilicity values result in proteins having uniform biological activity. As disclosed in U.S. Pat. No. 4,554,101, the following hydrophilicity values are assigned to respective amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); and tryptophan (−3.4).

Amino acid exchanges in proteins that do not totally change the activity of the molecule are known in the art. The most commonly occurring exchanges are exchanges between amino acid residues of Ala/Ser, Val/Ile, Asp/Glu, Thr/Ser, Ala/Gly, Ala/Thr, Ser/Asn, Ala/Val, Ser/Gly, Thr/Phe, Ala/Pro, Lys/Arg, Asp/Asn, Leu/Ile, Leu/Val, Ala/Glu and Asp/Gly.

When taking into consideration mutations having biologically equivalent activity, the antibody or a nucleotide molecule encoding the same according to the present invention is interpreted to include a sequence having substantial identity with the sequence set forth in the sequence number. The term "substantial identity" means that a sequence has a homology of at least 61%, preferably a homology of at least 70%, more preferably at least 80%, and most preferably at least 90%, when aligning the sequence of the present invention and any other sequence so as to correspond to each other as much as possible and analyzing the aligned sequence using algorithms commonly used in the art. Alignment methods for sequence comparison are well-known in the art.

The NCBI Basic Local Alignment Search Tool (BLAST) is accessible through NCBI or the like, and can be used in conjunction with sequence analysis programs such as BLASTP, BLASTM, BLASTX, TBLASTN and TBLASTX over the Internet. BLAST is available at www.ncbi.nlm.nih.gov/BLAST/. A method of comparing sequence homology using this program can be found at www.ncbi.nlm.nih.gov/BLAST/blast_help.html.

EXAMPLE

Hereinafter, the present invention will be described in more detail with reference to the following examples. However, it will be obvious to those skilled in the art that the following examples are provided only for illustration of the present invention and should not be construed as limiting the scope of the present invention based on the subject matter of the present invention.

Example 1: Confirmation of Fusion of Cell-Membrane-Like Substances with Cell Membrane In order to attach magnetic beads to the cell surface, whether or not a cell-membrane-like material, to which biotin is bound, was fused to the cell surface was confirmed using a flow cytometer as a pretreatment process. DHPE (1,2-dihexadecanoyl-sn-glycero-3-phosphoethanolamine) was used as the cell-membrane-like material (FIG. 2). The test was conducted using a fluorescent substance attached to DHPE, namely fluorescein DHPE (N-(fluorescein-5-thiocarbamoyl)-1,2-dihexadecanoyl-sn-glycero-3-phosphoethanolamine, triethylammonium salt, produced by Invitrogen Corporation), in various concentration conditions (1:250, 1:500, 1:1000, 1:2000), temperature conditions (room temperature, 4° C.), and reaction time conditions (30 minutes, 60 minutes).

First, HCC.95, a cancer cell line, was dispensed into 500,000 cells under each condition, and the reaction volume was 300 μl. The cultured sample was centrifuged at 1,500 rpm for 3 minutes with 1% FBS solution and was then washed to remove the supernatant. This was repeated twice. Then, the analysis was performed through a flow cytometer (FACS Aria III).

Figure 1:
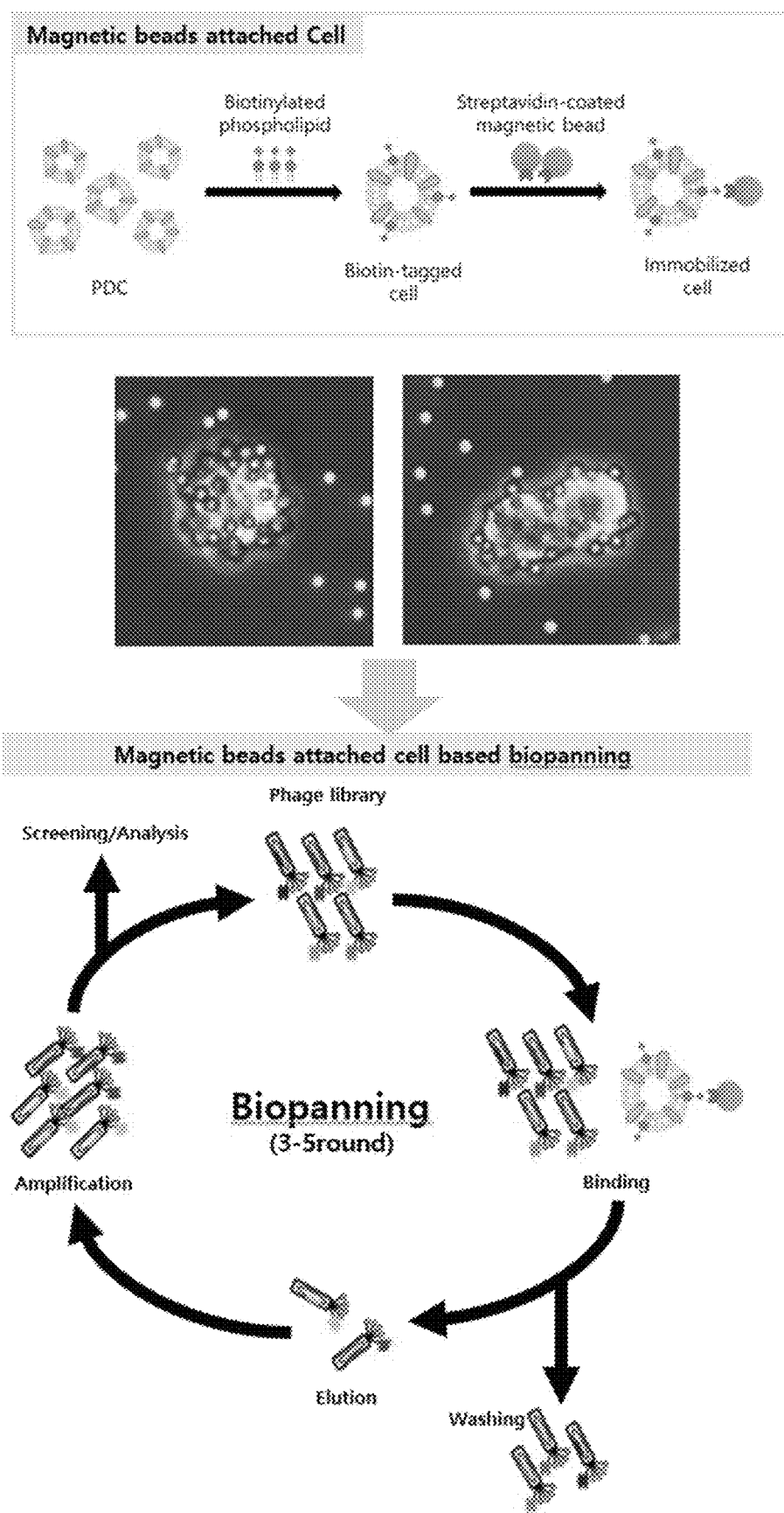
FIG. 1 is a schematic diagram showing the principle of a method according to the present invention.
Figure 3A:
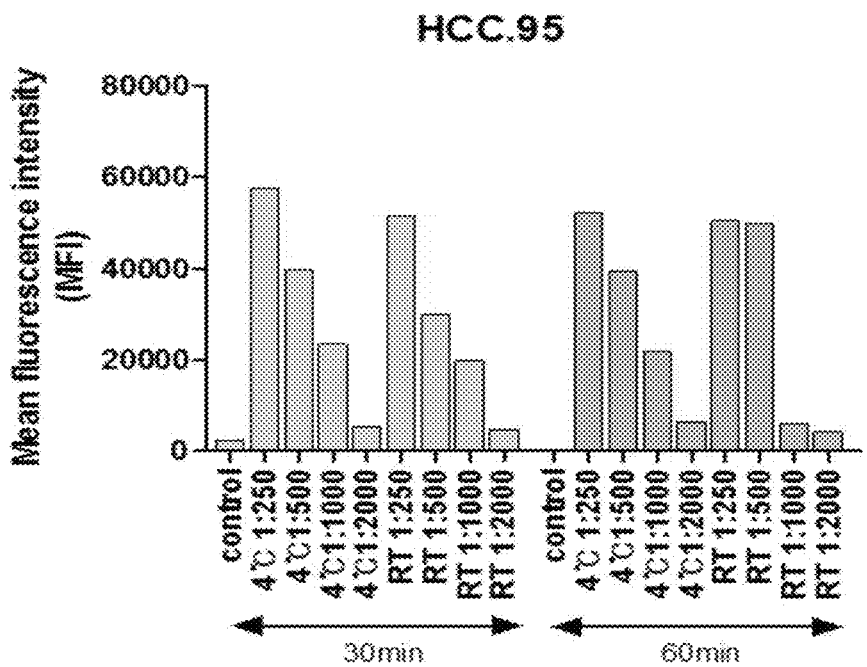
FIG. 3A shows the fluorescence intensity depending on reaction time (30 min, 60 min) in a cell containing a cell-membrane-like material according to an embodiment of the present invention
Figure 3B:
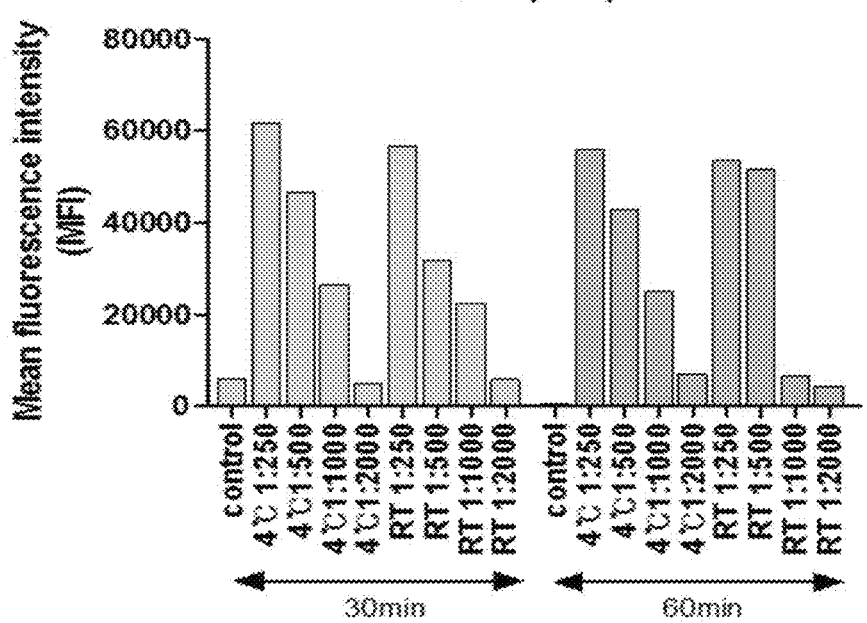
FIG. 3B shows that the cell of FIG. 3A contains the cell-membrane-like material even after 6 hours.

As a result, fluorescence intensity was observed to be proportional to concentration under all conditions (FIG. 3A). Based thereon, it was confirmed that a cell-membrane-like material was fused to the surface of viable cells, and that the result obtained by incubating the same sample at 4° C. for 6 hours and then measuring fluorescence intensity using a flow cytometer also showed the same pattern (FIG. 3B). This means that, even if a cell-membrane-like substance is fused to the cell membrane, the cell is stable.

Example 2: Confirmation and Optimization of Fusion of Biotin-Bound Cell-Membrane-Like Substances to Cell The test was conducted using the substance actually attached to the magnetic beads, namely BX DHPE (N-((6-(biotinoyl)amino)hexanoyl)-1,2-dihexadecanoyl-sn-glycero-3-phosphoethanolamine, triethylammonium salt, produced by Invitrogen Corporation), under various concentration conditions (0.5 mg/ml, 0.25 mg/ml, 0.125 mg/ml and 0.0625 mg/ml) (FIG. 4).

First, HCC.95, a cancer cell line, was dispensed into 500,000 cells under each condition, and the reaction volume was 300 μl. The cultured sample was centrifuged at 1,500 rpm for 3 minutes with 1% FBS solution and was then washed to remove the supernatant. This was repeated twice. Then, streptavidin-FITC (fluorescent material) having binding capacity specific to biotin was reacted at 4° C. for 1 hour. The cultured sample was centrifuged at 1,500 rpm for 3 minutes with a 1% FBS solution and was then washed to remove the supernatant. This was repeated twice. Then, analysis was performed using a flow cytometer (FACS Aria III).

Figure 5A:
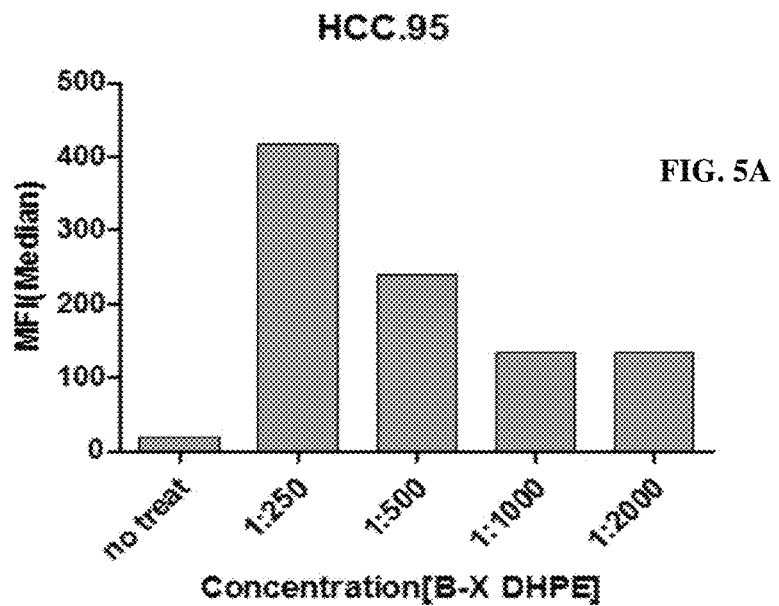
FIG. 5A shows binding efficiency depending on concentration of the cell-membrane-like material in the cell including the cell-membrane-like material according to an embodiment of the present invention.

As a result, fluorescence intensity having the same behavior as in Example 1 was confirmed (FIG. 5A).

In order to optimize conditions of fusion of the substance to the cell membrane, the test was conducted under various B-X DHPE concentration conditions (0.5 mg/ml, 0.25 mg/ml, 0.125 mg/ml and 0.0625 mg/ml), temperature conditions (4° C., room temperature), and reaction time conditions (30 minutes, 60 minutes), and sample preparation was performed in the same manner as above.

Figure 5B:
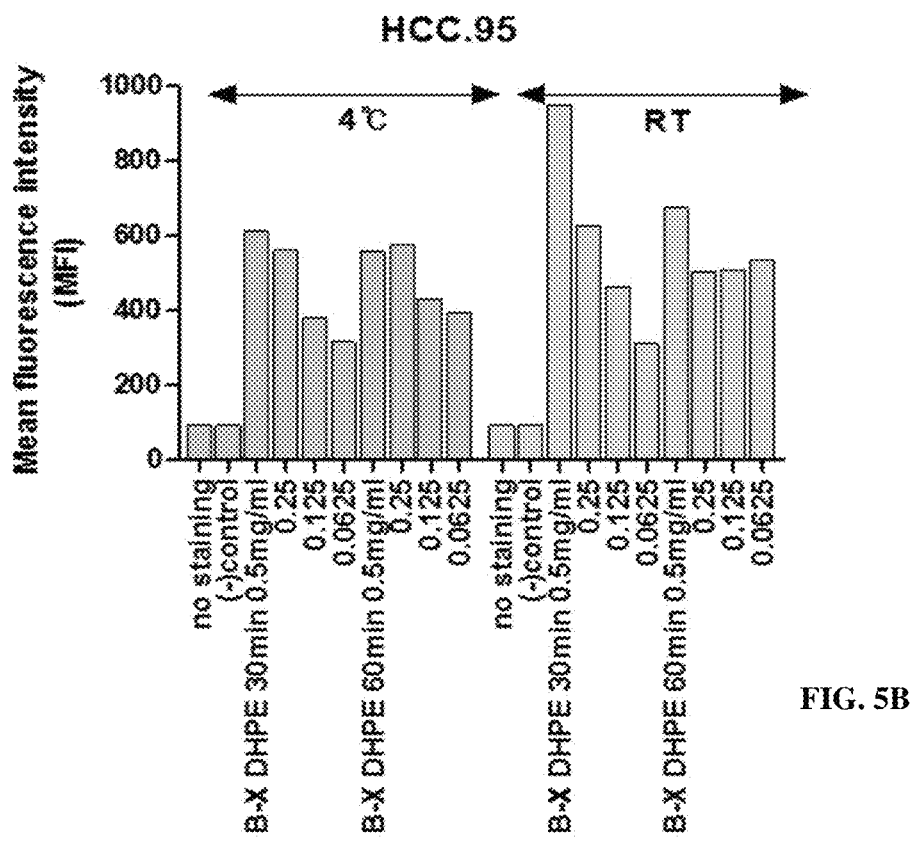
FIG. 5B shows the binding efficiency depending on concentration and reaction temperature.

As a result, it was confirmed that the fusion of the material to the cell membrane was the best at the B-X DHPE concentration (0.5 mg/ml), at room temperature, and for the reaction time of 30 minutes (FIG. 5B).

Example 3: Confirmation of Surface Protein Expression in Cells Fused with Cell-Membrane-Like Substance Although a cell-membrane-like substance is fused to a cell, it is not suitable for use in phage-display-based cell panning when there is a change in surface protein expression. Therefore, it was confirmed that the optimized conditions of B-X DHPE did not affect the cell surface protein, and the amount of B-X DHPE that fused to the cell surface was also confirmed.

GBM15-682T, a patient-derived cell, was used. This cell overexpresses the FGFR3 cell surface protein and thus is suitable for comparison of expression level. The expression level of the FGFR3 cell surface protein was measured through a flow cytometer under the condition in which the cell-membrane-like substance (B-X DHPE) was fused and under the condition in which the cell-membrane-like substance was not fused. GBM15-682T was dispensed into 500,000 cells under each condition, was used in a reaction volume of 300 μl, and reacted with B-X DHPE (0.5 mg/ml) at room temperature for 30 minutes. The cultured sample was centrifuged at 1,500 rpm for 3 minutes with 1% FBS solution and was then washed to remove the supernatant. This was repeated twice.

Then, the cell was treated with streptavidin-FITC (fluorescent material) and FGFR3-PE (fluorescent material) antibodies, respectively, and reacted at 4° C. for 1 hour. After performing washing as described above twice, B-X DHPE was analyzed through FITC fluorescence and FGFR3 was analyzed through PE fluorescence.

Figure 6A:
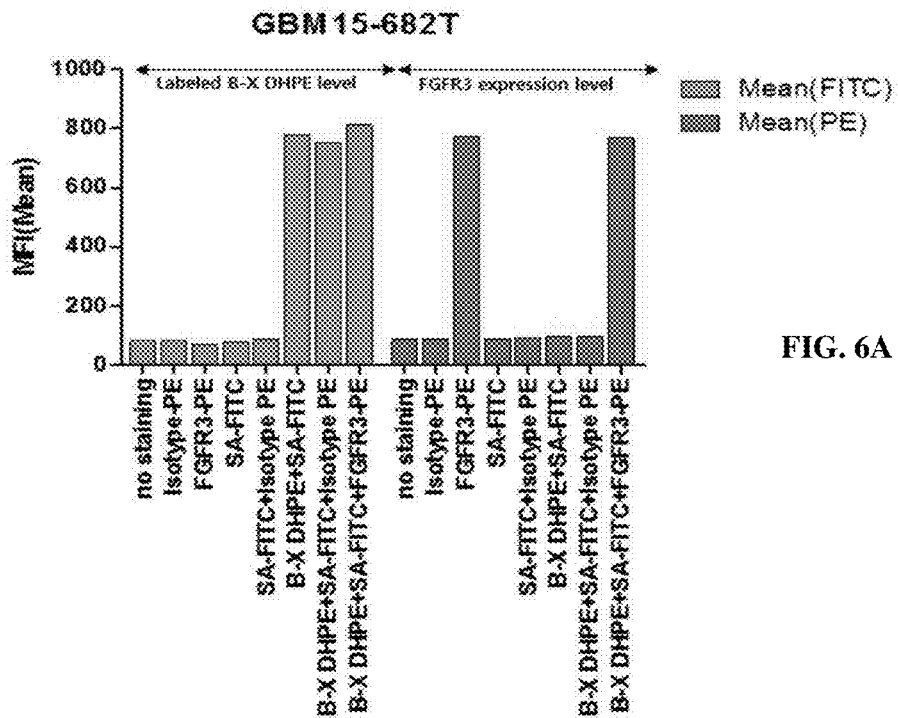
FIG. 6A shows the expression level of protein on the surface of the cell membrane depending on whether or not the cell-membrane-like material is fused.
Figure 6B:
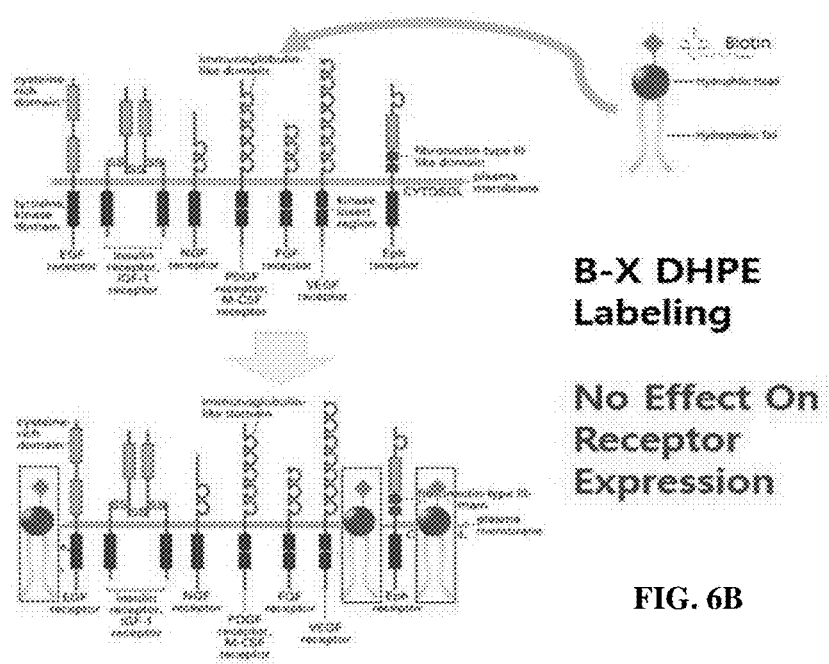
FIG. 6B is a schematic diagram showing the case where the cell-membrane-like material is bound to the cell membrane.

As a result, it was confirmed that there was no change in the level of B-X DHPE fused to the cell surface and the level of FGFR3 cell surface protein expressed (FIG. 6). That is, the result means that, although the cell-membrane-like substance (B-X DHPE) is fused to the cell membrane, it does not cause any alteration on the cell surface.

Example 4: Induction of Magnetization Through Attachment of Magnetic Beads to Cells Fused with Cell-Membrane-Like Substances and Optimization of Conditions 4-1: Confirmation of Effect of Complex-Binding Method B-X DHPE fused to cells contains a biotin component and thus has binding capacity specific to streptavidin. Therefore, it is possible to induce magnetism in cells using streptavidin-attached magnetic beads (Streptavidin Dynabeads: Dynabeads M-280 streptavidin; Invitrogen Corporation). As a method of inducing magnetization by attaching magnetic beads to cells, a direct method and an indirect method were compared. The direct method refers to a method of first reacting B-X DHPE with streptavidin Dynabeads and then fusing the result to cells, and the indirect method refers to a method of fusing B-X DHPE to the cells and then reacting the result with streptavidin Dynabeads.

The direct method was carried out as follows. 3.0 μg of B-X DHPE was reacted with 500 μg of streptavidin Dynabeads previously washed with a PBS (PH 7.4) buffer solution using a magnetic separator at room temperature for 30 minutes. Then, the result was washed twice with the same buffer solution using a magnetic separator. 1.0-5.0e+6 cells, previously washed with a PBS (pH 7.4) buffer solution, were cultured along with the previously reacted B-X DHPE and streptavidin Dynabead conjugate for 1 hour at room temperature. At this time, the reaction volume was set at 1 ml.

The indirect method was carried out as follows. 1.0-5.0E+6 cells washed with PBS (PH 7.4) buffer solution were cultured along with 3 μg of B-X DHPE for 30 minutes at room temperature. Then, the cells were washed twice with a PBS (pH 7.4) buffer solution using a magnetic separator. 500 μg of streptavidin Dynabeads previously washed with a PBS (pH 7.4) buffer solution using a magnetic separator were cultured along with B-X DHPE-fused cells at room temperature for 1 hour. The reaction volume was the same as in the direct method.

Figures 7A, 7B:
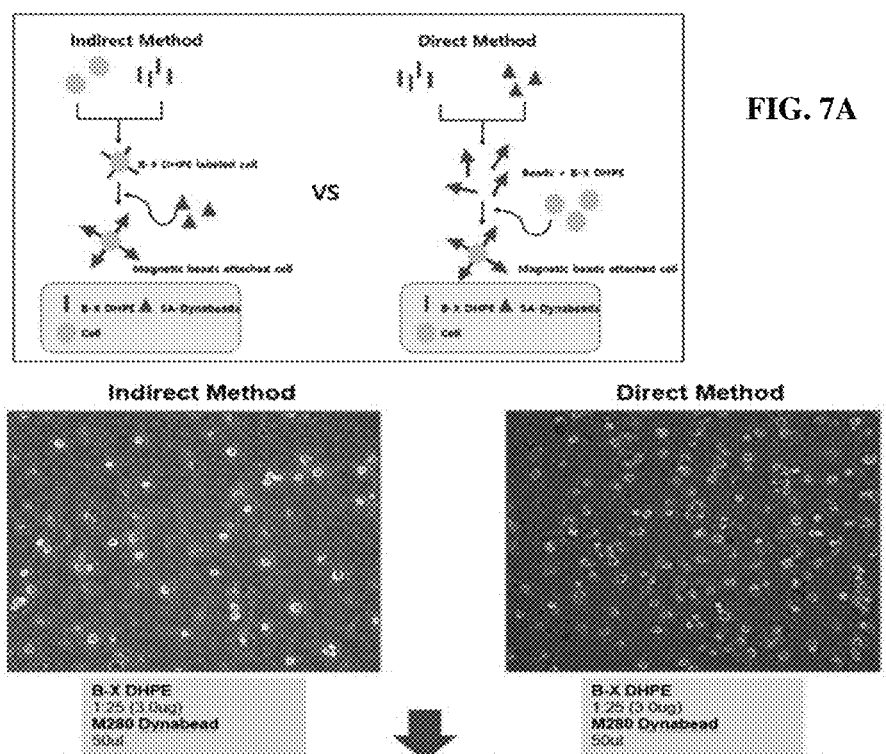
FIG. 7A is a schematic diagram showing a method of fusing the cell with the phospholipid/biotin/streptavidin/magnetic-bead complex according to an embodiment of the present invention.
FIG. 7B shows a result of observing the fusion efficiency of the two methods.

It was confirmed through the present invention that among the two methods, the direct method is capable of more easily attaching the magnetic beads to the cells (FIG. 7). That is, the direct method is effective in inducing magnetism of cells through magnetic beads.

4-2: Optimization of Magnetic-Bead Adhesion Rate

In order to increase the rate of adhesion of magnetic beads to cells, the reaction buffer solution was optimized. ① Culture medium, ② PBS (PH 7.4), ③ 2 mM EDTA/0.1% BSA, and ④ 0.1% Pluronic F-68 (Gibco) were applied to the direct method conducted above. The conjugate of B-X DHPE and streptavidin Dynabeads was cultured along with the pre-prepared cells under respective four buffer solution conditions above. After completion of the culture, each sample was transferred to a 6-well plate and analyzed under a microscope (20×, 40×).

Figure 8:
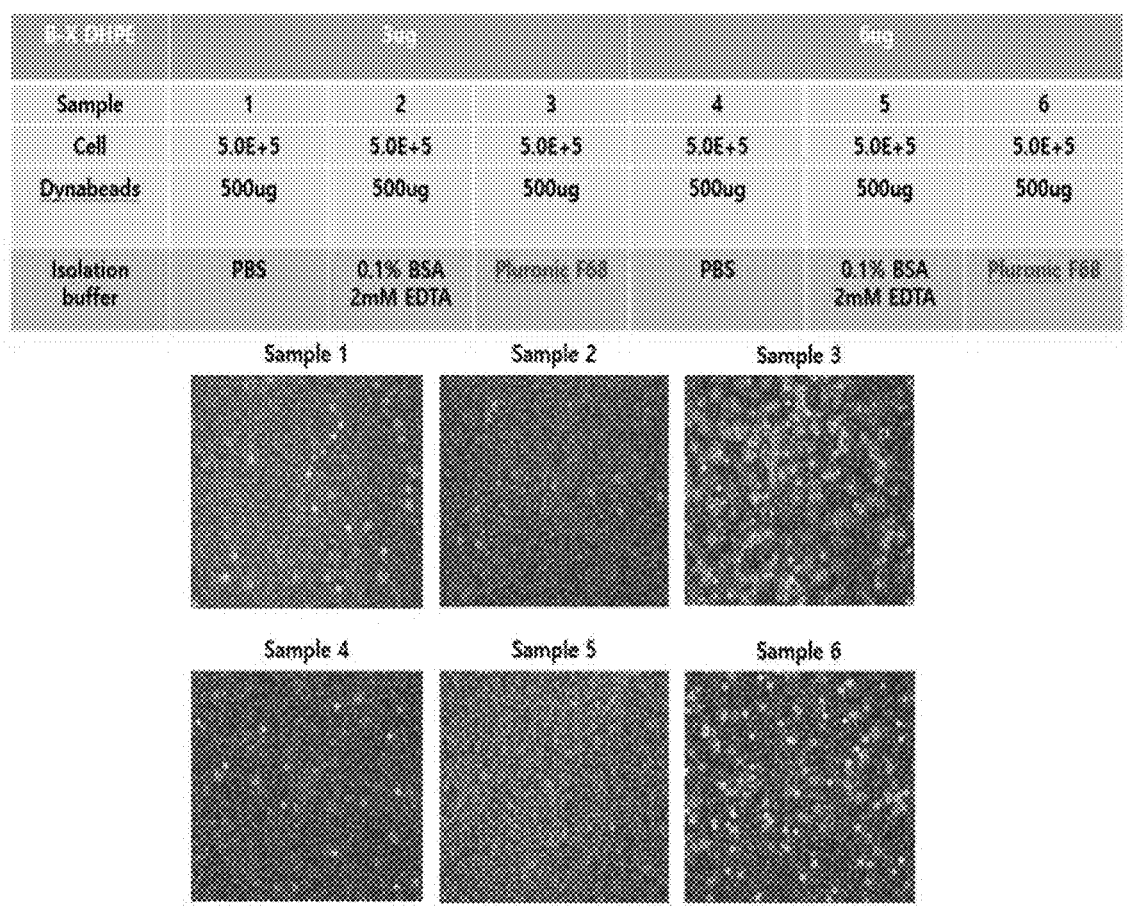
FIG. 8 shows a result of measuring the adhesion rate of magnetic beads depending on culture medium conditions according to an embodiment of the present invention.

As a result, it was confirmed that the culture conditions of 0.1% Pluronic F-68 exhibited a higher rate of adhesion of magnetic beads to cells (FIG. 8).

Figure 9:
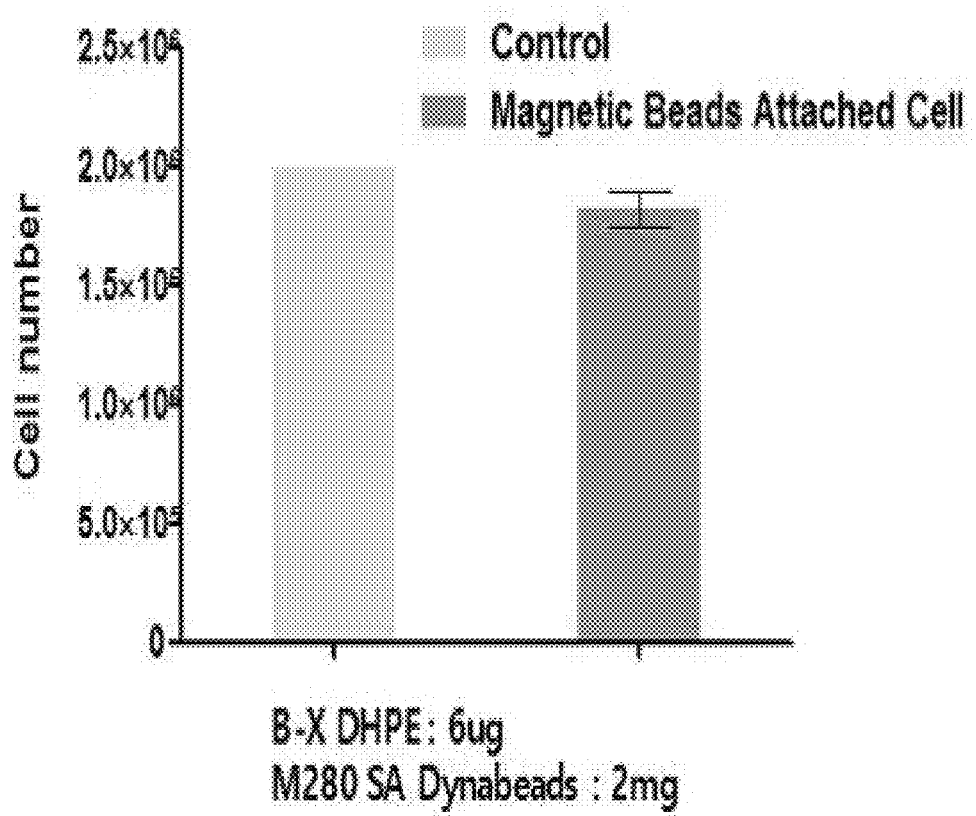
FIG. 9 shows a result of measuring the efficiency of formation of a phospholipid/biotin/streptavidin/magnetic-bead complex of the cell according to an embodiment of the present invention.

The number of cells in which magnetization is induced by the attachment of magnetic beads was measured using the number of cells used for actual cell panning. 2e+6 cells commonly used for cell panning were magnetized using 6 μg of B-X DHPE and 2 mg of streptavidin Dynabeads. After attaching the cells to the magnet by applying magnetism to the cells using a magnetism-based device (KingFisher Flex, Thermo Scientific) or a magnetic separator, the supernatant was removed, the cells were suspended again in 1 m of PBS (PH 7.4) buffer solution, and the number of cells was calculated with a C-Chip. Repeated experiments showed that about 90% or more of the cells were magnetized and interacted with the magnet (FIG. 9).

Example 5: Application of Magnetic-Bead-Attached Cells to Magnetism-Based Device and Automatic Cell Panning In the present invention, automatic cell panning was developed by fusing phage display technology using a magnetic-bead-attached cell through a magnetism-based device (KingFisher Flex, Thermo Scientific). Therefore, it was confirmed whether or not the cells to which the magnetic beads were attached were guided by the magnetism-based device or a magnetic separator and were moved or fixed through magnetism.

Figure 10:
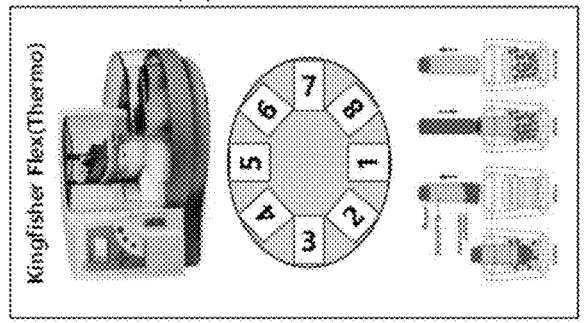
FIG. 10 shows a schematic diagram illustrating a magnetism-based automated cell-panning device and a step of operating the same.
Figure 11:
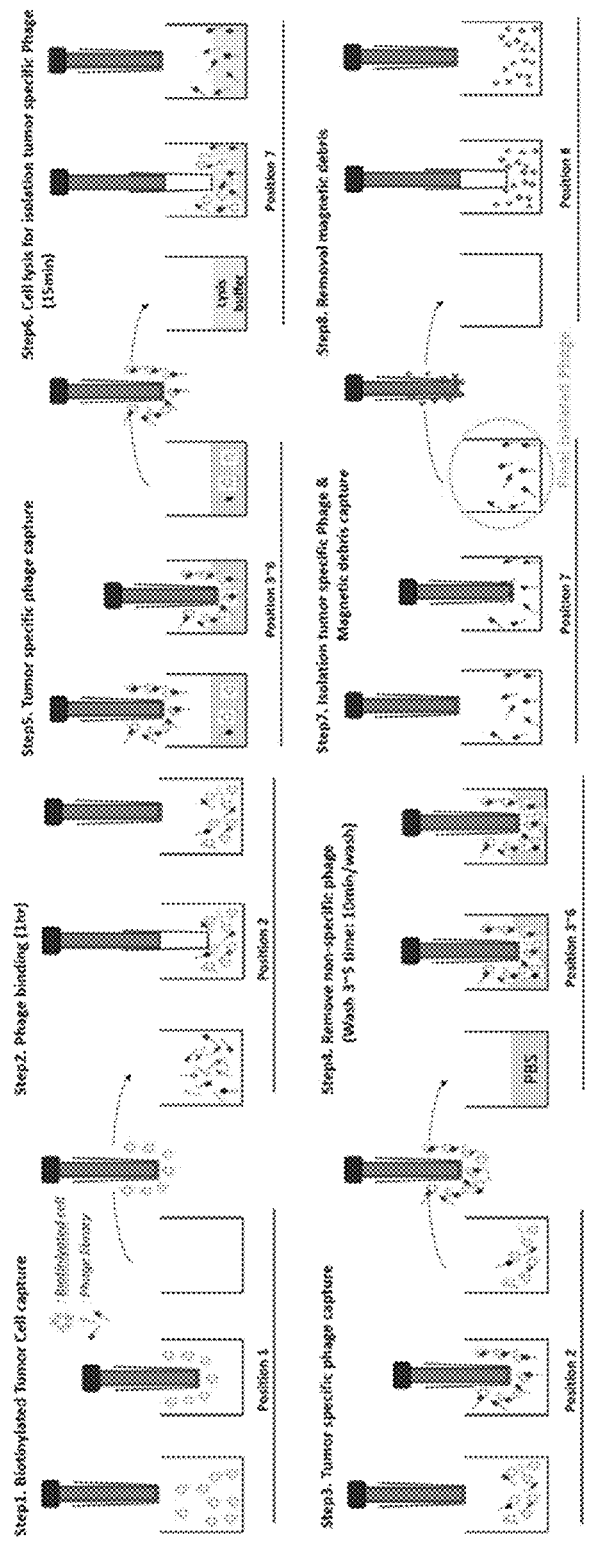
FIG. 11 shows a step of cell panning in an automated system using magnetic beads according to an embodiment of the present invention.

Magnetism-based devices can designate eight plate positions. After placing a plate having 24 deep wells at the eight plate positions, 1 ml of PBS was dispensed at each position. Then, the cells to which magnetic beads were attached were designated and seeded on the first plate, and were transferred from the first plate to the second plate with a magnetic rod of the device through software (BindIt 3.3 for KingFisher) for operation of the magnetism-based device. At this time, it was confirmed that the cells to which magnetic beads were attached were moved from the first plate to the second plate. This was repeatedly performed up to the eighth plate (FIGS. 10 and 11).

After completion, the number of cells remaining in the PBS (pH 7.4) buffer solution of each plate was measured by a C-Chip. In addition, the number of cells that finally moved to the eighth plate was compared with the number of cells remaining after the general cell-panning method.

The result showed that the number of cells remaining after the cell-panning method through a magnetism-based device was similar to the number of cells remaining after the cell-panning method performed directly by an experimenter (FIG. 12).

Automatic cell panning enables simultaneous panning of 24 to 96 cells and realization of a high-speed mass screening system. In addition, binding, washing, elution and lysis conditions can be flexibly controlled in each panning step, and the time taken therefor can be shortened.

Example 6: Attachment of Magnetic Beads to Antigen-Overexpressing Patient-Derived Cells and Application of Automatic Cell Panning Through Magnetism-Based Device Using the Same Magnetic beads were attached to viable cells through the experimental method developed in the present invention, and automatic cell panning was performed thereon using a magnetism-based device. The antigen used in this example was fibroblast growth factor receptor 3 (FGF3), and the recombinant antigen used in this example was recombinant human FGF R3 (IIIc), an Fc chimera protein produced by R&D Systems.

First, bio-panning was performed four times (rounds) by a commonly and generally known method of fixing an antigen on an immunotube to obtain a phage pool in which antigen-specific phages are amplified through the fourth iteration of bio-panning, automatic cell panning was conducted once (one round) using the phage pool and a magnetism-based device under strong washing conditions (wash strength set to Fast in the Wash step in BindIt Software 3.3.1, KingFisher Flex equipment software) and weak washing conditions (wash strength set to Medium or Slow in the wash step), and then the result of cell panning was counted and recovered.

Next, automatic panning was performed four times through recombinant protein-based magnetic bead panning using a KingFisher Flex magnetism-based device, (ThermoFisher Scientific, USA) to obtain a phage pool in which antigen-specific phages are amplified through the fourth iteration of bio-panning, automatic cell panning through a magnetism-based device was conducted once using the phage pool under weak washing conditions (wash strength set to Medium or Slow in the wash step), and then the result of cell panning was counted and recovered.

In order to recover and count phages that have more specific binding capacity to certain antigen structures expressed on the actual cell surface from the pool recovered under normal conditions and the pool recovered through automated panning, magnetic-bead-attached cell panning was performed automatically using a magnetism-based device through the panning method developed in the present invention.

Patient-derived cells PDC #1, overexpressing an antigen, and patient-derived cells PDC #2, under-expressing an antigen, were used for automatic cell panning. First, PDC #2 (2×10E+6 cells/library) under-expressing an antigen previously washed with PBS, and previously washed magnetic beads (Dynabeads) were reacted with the phage pool amplified in the antigen four times at room temperature for 1 hour, and then the sample was centrifuged to recover only the supernatant and to remove phages non-specific for the antigen and phages non-specific for magnetic beads.

Figure 13B:
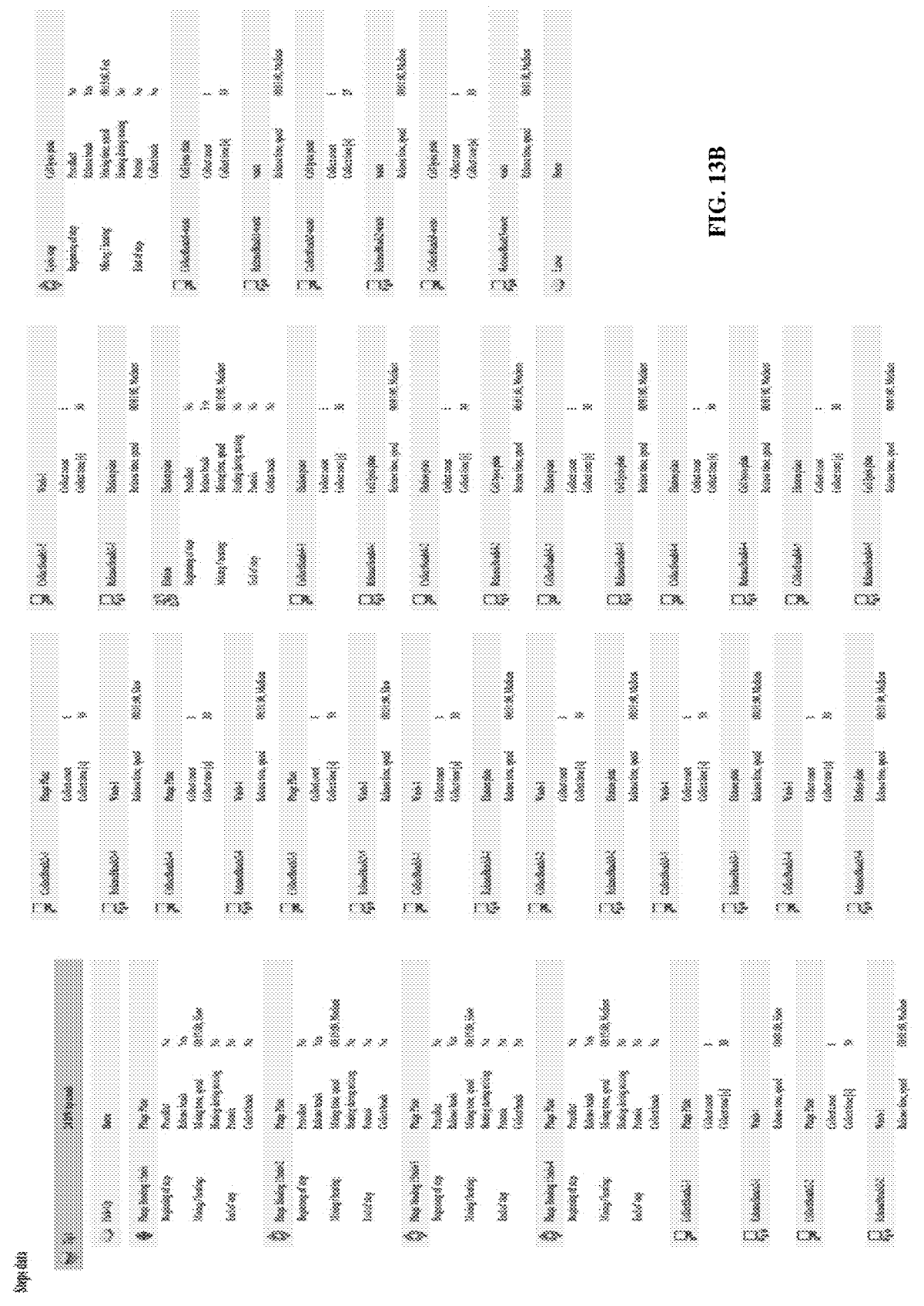

The recovered supernatant was introduced into an automated device (KingFisher Flex, Thermo Scientific, USA) along with magnetic-bead-attached patient-derived cells through the method developed in the present invention, and the corresponding operating software protocol is shown in FIG. 13.

The phages recovered by automatic cell panning were infected into TG1 host cells and counted in an LB/ampicillin culture medium. To determine the amount of phages that were recovered, the recovered solution was diluted and infected into host cells and then spread in an LB/ampicillin agar medium and quantified through the number of colonies the next day (FIG. 14). The remaining recovered solution was spread on a 15 cm culture medium and cultured, and then 5 ml of SB culture medium (50% glycerol) was added thereto to recover and store the colonies (−80° C.)

Example 7: ELISA-Based Antibody Screening Results with Binding Capacity Specific to Certain Antigen Using Automatic Panning Results FGFR3-specific antibodies were selected through conventional and general scFv ELISA screening. Host cells (TG1) were infected with the phage pool recovered by automatic cell panning under each condition and a single colony was obtained therefrom and then was used for ELISA verification. Each single colony was inoculated in a well filled with 200 μl of SB/ampicillin on a 96-well plate (37° C., 3 hours) and the culture medium was treated with a final concentration of 1 mM IPTG to induce protein expression, and then cultured at 28° C. for 16 hours or more.

The next day, the culture plate was treated with a TES solution (20% w/v sucrose, 50 mM Tris, 1 mM EDTA, pH 8.0) to collect scFv present around the surrounding cytoplasmic region of *E. Coli* host cells left in each well after centrifugation and removal of the supernatant and allowed to stand at 4° C., and then the supernatant was recovered through a centrifuge, treated on a 96-well plate coated with a specific antigen in advance, and reacted at room temperature for 1 hour. After the reaction, a washing process was conducted and treatment with anti-HA HRP along with a blocking buffer was performed for 1 hour, the same washing process was performed, and then treatment with a TMB substrate was performed and analysis was performed with O.D. of 450 nm.

Figure 16:
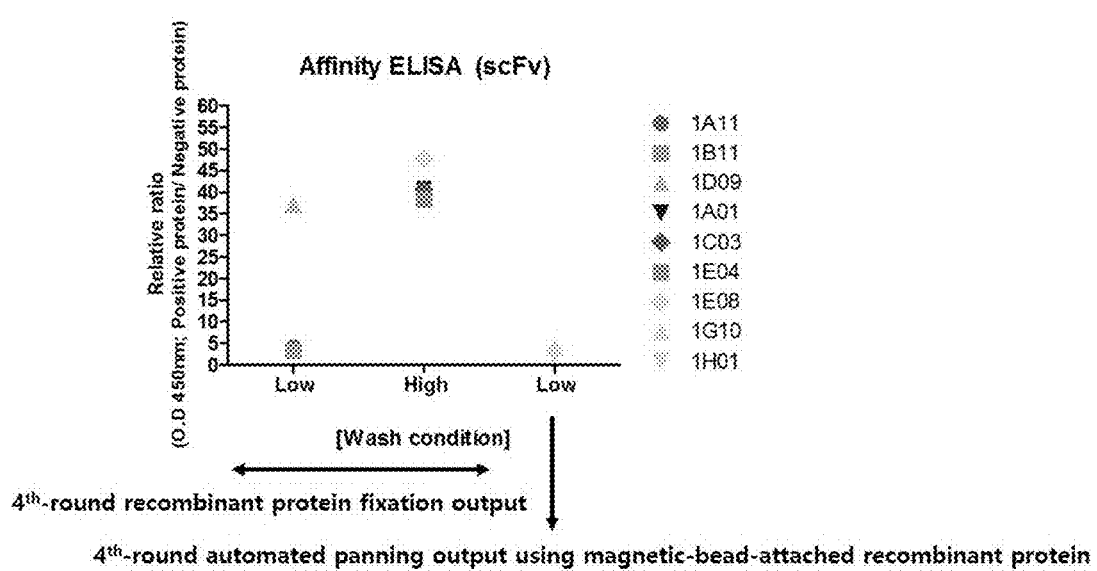
FIG. 16 is a graph showing relative values for positive/negative recombinant proteins as a result of comparing ELISA values of the selected antibodies.

As a result, as can be seen from FIG. 16, scFvs that are more specific for FGFR3 expressed on the actual cell surface and more structurally stable could be automatically selected from the scFv pool having binding capacity specific for FGFR3 obtained through biopanning using a recombinant protein, and antibodies specific for various libraries and various antigens or cells could be automatically selected through a magnetism-based device.

Although specific configurations of the present invention have been described in detail, those skilled in the art will appreciate that this description is provided to set forth preferred embodiments for illustrative purposes and should not be construed as limiting the scope of the present invention. Therefore, the substantial scope of the present invention is defined by the accompanying claims and equivalents thereto.

INDUSTRIAL APPLICABILITY

The method of attaching magnetic beads to viable cells according to the present invention is a method that can be applied to bio-panning based on phage display using magnetism-induced cells. The method is capable of selecting antibodies while maintaining the structure of the cell surface protein, and has a higher possibility of selecting antigen-specific antibodies than a panning method using recombinant proteins. In addition, the method is capable of selecting antibodies against a large number of various antigens with little labor through application to a magnetism-based high-speed mass-screening device and system.

The invention claimed is:

1. A method for screening an antibody or antigen-binding fragment thereof binding to an antigenic protein, the method comprising:
  (i) inducing magnetism of a cell overexpressing the antigenic protein by fusing a phospholipid/biotin/streptavidin/magnetic-bead complex, prepared by reacting a biotinylated phospholipid with streptavidin and magnetic beads, to the cell in which the biotinylated phospholipid is inserted into the cell membrane and bound to the streptavidin/magnetic-bead complex, or by treating a streptavidin/magnetic-bead complex to the cell in which a biotinylated phospholipid is inserted into the cell membrane prepared by culturing the cell in the presence of the biotinylated phospholipid to obtain the cell in which the biotinylated phospholipid is bound to the streptavidin/magnetic-bead complex;
  (ii) treating the cell with a library comprising an antibody or antigen-binding fragment thereof and screening an antibody or antigen-binding fragment thereof binding to the antigenic protein using the magnetism;
  (iii) reacting the antibody or antigen-binding fragment thereof screened from the library with a cell not expressing the antigenic protein to select only the antibody or antigen-binding fragment thereof specifically binding to the antigenic protein; and
  (iv) removing an antibody or antigen-binding fragment thereof binding to the cell not expressing the antigenic protein from the selected antibody or antigen-binding fragment thereof, thereby obtaining the antibody or antigen-binding fragment thereof binding to the antigenic protein.

2. The method according to claim 1, wherein the phospholipid comprises any one selected from the group consisting of PE (phosphoethanolamine)-based phospholipids, PA (phosphatidic acid)-based phospholipids, PG (phosphatidylglycerol)-based phospholipids, PS (phosphatidylserine)-based phospholipids, PI (phosphatidylinositol)-based phospholipids, sphingolipid-based phospholipids and sterol-based phospholipids.

3. The method according to claim 2, wherein the phospholipid comprises any one selected from the group consisting of DHPE (1,2-dihexadecanoyl-sn-glycero-3-phosphoethanolamine), fluorescein DHPE (N-(fluoresceine-5-thiocarbamoyl)-1-2-dihexadecanoyl-sn-glycero-3-phosphoethanolamine), B-X DHPE (N-((6-(biotinoyl)amino)hexanoyl)-1-2-dihexadecanoyl-sn-glycero-3-phosphoethanolamine), Biotin PE(1-oleoyl-2-(12-biotinyl(aminododecanoyl))-sn-glycero-3-phosphoethanolamine), biotin PS (1-oleoyl-2-(12-biotinyl(aminododecanoyl))-sn-glycero-3-phospho-L-serine (ammonium salt)) and biotin PC (1-oleoyl-2-[12-biotinyl(aminododecanoyl)]-sn-glycero-3-phosphocholine).

4. The method according to claim 1, wherein the cell overexpressing an antigenic protein, in which a biotinylated phospholipid is inserted into a membrane of the cell and the biotinylated phospholipid is bound to the streptavidin/magnetic-bead complex, is prepared through a process comprising:
  (a) culturing a cell overexpressing an antigen protein in presence of biotinylated phospholipid to obtain a cell in which the biotinylated phospholipid is inserted into the cell membrane; and
  (b) treating the biotinylated phospholipid of the obtained cell with a streptavidin/magnetic-bead complex to obtain a cell in which the biotinylated phospholipid is inserted into the cell membrane and in which the biotinylated phospholipid is bound to the streptavidin/magnetic-bead complex.

5. The method according to claim 1, wherein the cell overexpressing an antigenic protein, in which a biotinylated phospholipid is inserted into a membrane of the cell and the biotinylated phospholipid is bound to the streptavidin/magnetic-bead complex, is prepared through a process comprising:
  (a) reacting biotinylated phospholipid with streptavidin and magnetic beads to prepare a phospholipid/biotin/streptavidin/magnetic-bead complex; and
  (b) fusing the phospholipid/biotin/streptavidin/magnetic-bead complex to a cell overexpressing an antigen protein to obtain a cell overexpressing an antigen protein in which the biotinylated phospholipid is inserted into the cell membrane and in which the biotinylated phospholipid is bound to the streptavidin/magnetic-bead complex.

6. The method according to claim 1, wherein the cell is bound to the streptavidin/magnetic-bead complex in a medium containing a surfactant.

7. The method according to claim 6, wherein the surfactant comprises any one selected from the group consisting of alkyl polyglycoside, cetyl alcohol, decyl glucoside, decyl polyglucoside, maltosides, NP-40, oleyl alcohol, poloxamer, polysorbate, sorbitan, Triton X-100 and Tween 80.

8. The method according to claim 1, wherein the magnetism-based system is a device for separating cells using magnetism.

9. The method according to claim 1, wherein the antibody or antigen-binding fragment thereof is an antibody or antigen-binding fragment thereof that is internalized into a cell.

10. The method according to claim 1, further comprising producing IgG from the antibody or antigen-binding fragment thereof selected according to the method.

* * * * *